US008922633B1

(12) United States Patent
Pfeffer

(10) Patent No.: US 8,922,633 B1
(45) Date of Patent: Dec. 30, 2014

(54) DETECTION OF GASTROINTESTINAL SECTIONS AND TRANSITION OF AN IN-VIVO DEVICE THERE BETWEEN

(75) Inventor: Yehuda Pfeffer, Migdal Haemek (IL)

(73) Assignee: Given Imaging Ltd., Yoqneam (IL)

( * ) Notice: Subject to any disclaimer, the term of this patent is extended or adjusted under 35 U.S.C. 154(b) by 378 days.

(21) Appl. No.: 13/245,273

(22) Filed: Sep. 26, 2011

Related U.S. Application Data

(60) Provisional application No. 61/386,821, filed on Sep. 27, 2010.

(51) Int. Cl.
A61B 1/04 (2006.01)
H04N 7/18 (2006.01)
A61B 1/00 (2006.01)
A61B 1/06 (2006.01)

(52) U.S. Cl.
CPC ............... A61B 1/041 (2013.01); H04N 7/183 (2013.01); H04N 7/18 (2013.01); A61B 1/06 (2013.01); A61B 1/00009 (2013.01); A61B 1/00016 (2013.01)
USPC ............................................ 348/65; 382/128

(58) Field of Classification Search
CPC .... H04N 7/183; A61B 1/00016; A61B 1/041; A61B 1/06; A61B 1/00009
See application file for complete search history.

(56) References Cited

U.S. PATENT DOCUMENTS

| 4,854,328 | A | 8/1989 | Pollack |
| 5,209,220 | A | 5/1993 | Hiyama et al. |
| 5,331,551 | A | 7/1994 | Tsuruoka et al. |
| 5,572,252 | A | 11/1996 | Naka et al. |
| 5,596,366 | A | 1/1997 | Takashima et al. |
| 5,604,531 | A | 2/1997 | Iddan et al. |
| 5,647,368 | A | 7/1997 | Zeng et al. |
| 5,649,021 | A | 7/1997 | Matey et al. |
| 5,738,110 | A | 4/1998 | Beal et al. |
| 5,833,603 | A | 11/1998 | Kovacs et al. |
| 5,873,830 | A | 2/1999 | Hossack et al. |
| 6,053,873 | A | 4/2000 | Govari et al. |

(Continued)

FOREIGN PATENT DOCUMENTS

| GB | 2 374149 | 10/2002 |
| WO | WO 02082979 | 10/2002 |

OTHER PUBLICATIONS

Igual et al., Automatic Discrimination of Duodenum in Wireless Capsule Video Endoscopy, ECIFMBE 2008, IFMBE Proceedings 22, pp. 1536-1539, 2008.*

(Continued)

Primary Examiner — Joseph Ustaris
Assistant Examiner — Jill Sechser
(74) Attorney, Agent, or Firm — Pearl Cohen Zedek Latzer Baratz LLP

(57) ABSTRACT

An in-vivo device may capture images of the GI system and transfer frames to an external system for analysis. As frames are transferred from the in-vivo device to the external system each frame may be scored as belonging to a first GI section or to a second GI section, and the frame scores may be buffered in a score buffer. Based on shifting of a reference function across the buffered frame scores and calculating distances between the buffered frame scores and the shifted reference function, the time at which the in-vivo device transitions from the first section of the GI system to the second section of the GI section may be determined.

20 Claims, 9 Drawing Sheets

(56) References Cited

U.S. PATENT DOCUMENTS

| | | | |
|---|---|---|---|
| 6,157,677 A | 12/2000 | Martens et al. | |
| 6,402,689 B1 | 6/2002 | Scarantino et al. | |
| 6,428,469 B1 | 8/2002 | Iddan et al. | |
| 6,635,834 B1 | 10/2003 | Wenner | |
| 6,654,504 B2 | 11/2003 | Lubin et al. | |
| 6,709,387 B1 | 3/2004 | Glukhovsky et al. | |
| 6,900,790 B1 | 5/2005 | Doi et al. | |
| 6,947,788 B2 | 9/2005 | Gilboa et al. | |
| 6,950,690 B1 | 9/2005 | Meron et al. | |
| 7,009,634 B2 | 3/2006 | Iddan et al. | |
| 7,022,067 B2 | 4/2006 | Glukhovsky et al. | |
| 7,136,518 B2 | 11/2006 | Griffin et al. | |
| 7,190,818 B2 | 3/2007 | Ellis et al. | |
| 7,221,388 B2 | 5/2007 | Sudo et al. | |
| 7,228,166 B1 | 6/2007 | Kawasaki et al. | |
| 7,232,410 B2 | 6/2007 | Takahashi | |
| 7,236,623 B2 | 6/2007 | Chapoulaud et al. | |
| 7,287,105 B1* | 10/2007 | Owen et al. | 710/52 |
| 7,295,226 B1 | 11/2007 | Meron et al. | |
| 7,316,647 B2 | 1/2008 | Kimoto et al. | |
| 7,319,781 B2 | 1/2008 | Chen et al. | |
| 7,672,497 B2 | 3/2010 | Nicponski | |
| 7,684,599 B2 | 3/2010 | Horn et al. | |
| 7,885,446 B2 | 2/2011 | Horn et al. | |
| 7,953,261 B2 | 5/2011 | Nishimura et al. | |
| 8,768,024 B1 | 7/2014 | Zingman et al. | |
| 2001/0035902 A1 | 11/2001 | Iddan et al. | |
| 2001/0051766 A1 | 12/2001 | Gazdzinski | |
| 2002/0042562 A1 | 4/2002 | Meron et al. | |
| 2002/0103425 A1 | 8/2002 | Mault | |
| 2002/0173718 A1 | 11/2002 | Frisch et al. | |
| 2002/0198439 A1 | 12/2002 | Mizuno | |
| 2003/0016864 A1 | 1/2003 | McGee et al. | |
| 2003/0020810 A1 | 1/2003 | Takizawa | |
| 2003/0077223 A1 | 4/2003 | Glukhovsky et al. | |
| 2003/0142753 A1 | 7/2003 | Gunday | |
| 2004/0010375 A1 | 1/2004 | Schomacker et al. | |
| 2004/0073087 A1 | 4/2004 | Glukhovsky et al. | |
| 2004/0111011 A1 | 6/2004 | Uchiyama et al. | |
| 2004/0115877 A1 | 6/2004 | Iddan | |
| 2004/0180391 A1 | 9/2004 | Gratzl et al. | |
| 2004/0225223 A1 | 11/2004 | Honda et al. | |
| 2004/0249291 A1 | 12/2004 | Honda et al. | |
| 2004/0264754 A1 | 12/2004 | Kleen et al. | |
| 2005/0074151 A1 | 4/2005 | Chen et al. | |
| 2005/0075537 A1 | 4/2005 | Chen et al. | |
| 2005/0075551 A1 | 4/2005 | Horn et al. | |
| 2005/0148816 A1 | 7/2005 | Glukhovsky et al. | |
| 2005/0148847 A1* | 7/2005 | Uchiyama et al. | 600/407 |
| 2005/0171418 A1 | 8/2005 | Lin | |
| 2005/0196023 A1 | 9/2005 | Chen et al. | |
| 2005/0215876 A1 | 9/2005 | Chen et al. | |
| 2005/0228293 A1 | 10/2005 | Cahill et al. | |
| 2005/0266074 A1 | 12/2005 | Zilberstein et al. | |
| 2005/0281446 A1 | 12/2005 | Glukhovsky et al. | |
| 2005/0288594 A1 | 12/2005 | Lewkowicz et al. | |
| 2006/0050966 A1 | 3/2006 | Nishimura et al. | |
| 2006/0069317 A1* | 3/2006 | Horn et al. | 600/300 |
| 2006/0155174 A1 | 7/2006 | Glukhovsky et al. | |
| 2006/0164511 A1 | 7/2006 | Krupnik | |
| 2006/0193505 A1 | 8/2006 | Glukhovsky et al. | |
| 2006/0217593 A1 | 9/2006 | Gilad et al. | |
| 2006/0239557 A1 | 10/2006 | Cahill et al. | |
| 2007/0053557 A1 | 3/2007 | Cahill et al. | |
| 2007/0104272 A1 | 5/2007 | He et al. | |
| 2007/0135715 A1 | 6/2007 | Inoue et al. | |
| 2007/0165924 A1 | 7/2007 | Nicponski | |
| 2007/0165932 A1 | 7/2007 | Nishimura et al. | |
| 2007/0165942 A1 | 7/2007 | Jin et al. | |
| 2007/0230893 A1 | 10/2007 | Meron et al. | |
| 2007/0255095 A1 | 11/2007 | Gilreath et al. | |
| 2007/0292011 A1 | 12/2007 | Nishimura et al. | |
| 2008/0051642 A1 | 2/2008 | Krupnik | |
| 2008/0147087 A1 | 6/2008 | Horn et al. | |
| 2008/0242931 A1 | 10/2008 | Nishino | |
| 2009/0148058 A1 | 6/2009 | Dane et al. | |
| 2009/0196476 A1 | 8/2009 | Inoue | |
| 2010/0046816 A1 | 2/2010 | Igual-Munoz et al. | |

OTHER PUBLICATIONS

Office Action issued by the United States Patent and Trademark Office for U.S. Appl. No. 12/543,977 dated Apr. 16, 2012.

Office Action issued by the United States Patent and Trademark Office for U.S. Appl. No. 12/543,977 dated Aug. 23, 2012.

Office Action for U.S. Appl. No. 11/235,541 mailed on Sep. 8, 2008.

Final Office Action for U.S. Appl. No. 11/235,541 mailed on Feb. 25, 2009.

Notice of Allowance for U.S. Appl. No. 11/235,541 mailed on Aug. 21, 2009.

Notice of Allowance for U.S. Appl. No. 11/235,541 mailed on Dec. 30, 2009.

Medscape Gastroenterology, "A Mosaic Pattern of the Descending Duodenum", Medscape Gastroenterology, vol. 2, No. 1, Medscape, <URL:http://www.medscape.com/viewarticle/405488_2>, retrieved Jun. 2, 2008.

Berens et al., "Stomach, Intestine and Colon Tissue Discriminators for Wireless Capsule Endoscopy Images", Proc of SPIE, vol. 5747, pp. 283-290, 2005.

Office Action for U.S. Appl. No. 12/719,601 mailed on Jun. 22, 2010.

Notice of Allowance for U.S. Appl. No. 12/719,601 mailed on Oct. 7, 2010.

Office Action of U.S. Appl. No. 11/235,541 dated Sep. 8, 2008.

Notice of Allowance of U.S. Appl. No. 11/235,541 dated Dec. 30, 2009.

Notice of Allowance of U.S. Appl. No. 11/235,541 dated Aug. 21, 2009.

Final Office Action of U.S. Appl. No. 11/235,541 dated Feb. 25, 2009.

Office Action of U.S. Appl. No. 12/719,601 dated Jun. 22, 2010.

Notice of Allowance of U.S. Appl. No. 12/719,601 dated Oct. 7, 2010.

Office Action of U.S. Appl. No. 12/543,977 dated Apr. 16, 2012.

Final Office Action of U.S. Appl. No. 12/543,977 dated Aug. 23, 2012.

Office Action of U.S. Appl. No. 13/907,076 dated Oct. 3, 2013.

Notice of Allowance of U.S. Appl. No. 13/907,076 dated Feb. 27, 2014.

* cited by examiner

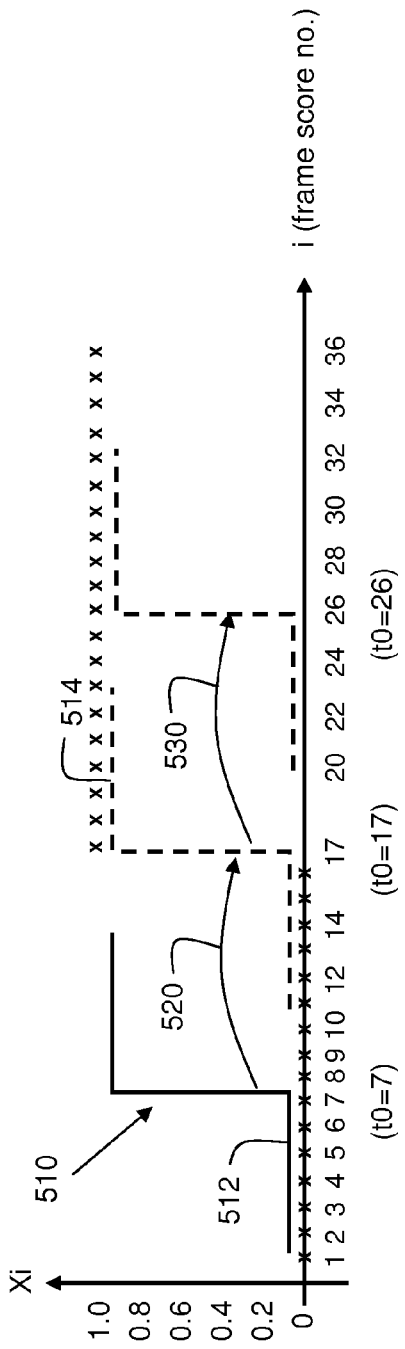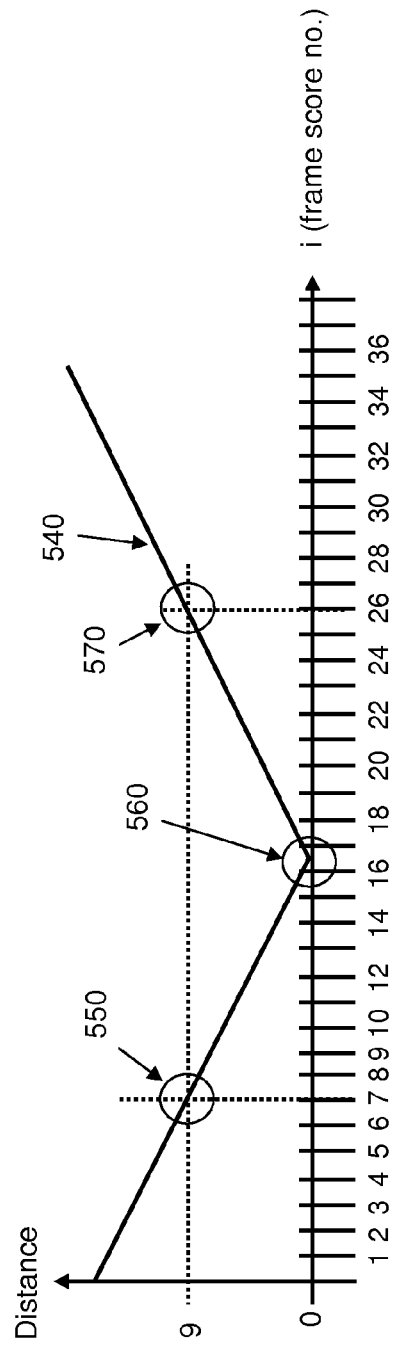
Fig. 5A
Fig. 5B

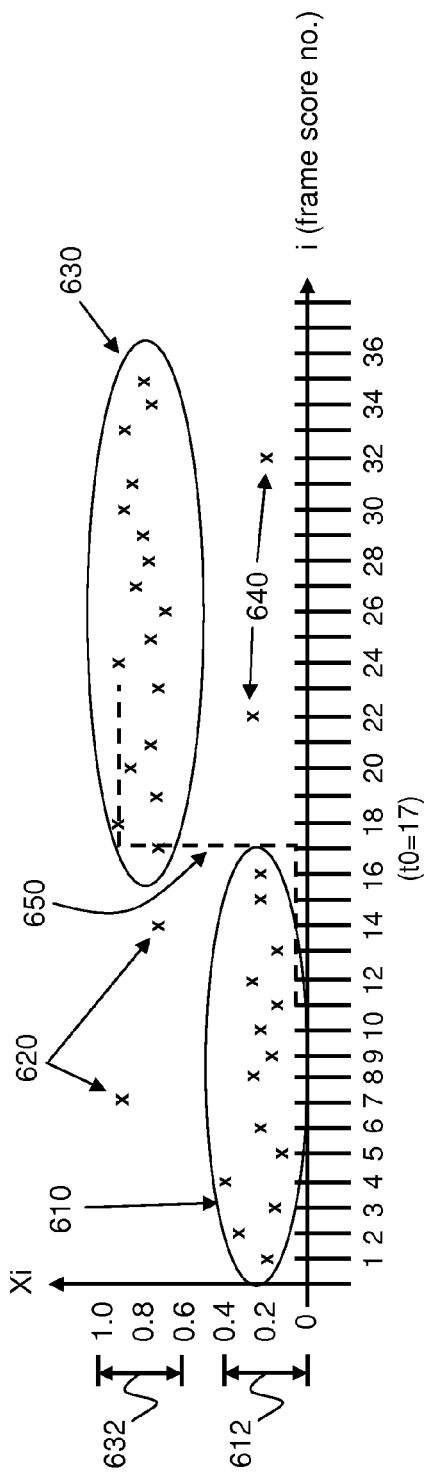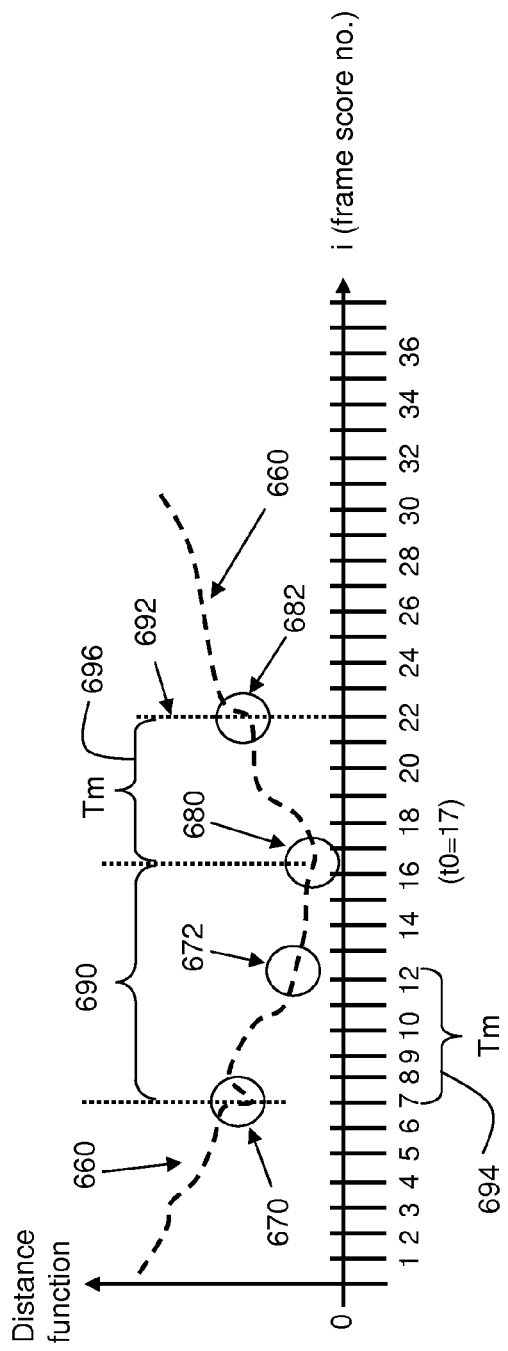
Fig. 6A
Fig. 6B

DETECTION OF GASTROINTESTINAL SECTIONS AND TRANSITION OF AN IN-VIVO DEVICE THERE BETWEEN

PRIOR APPLICATION DATA

The present application claims the benefit of prior U.S. provisional patent application Ser. No. 61/386,821, filed Sep. 27, 2010, entitled "DETECTION OF GASTROINTESTINAL SECTIONS AND TRANSITION OF AN IN-VIVO DEVICE THERE BETWEEN", incorporated by reference herein in its entirety.

FIELD OF THE INVENTION

The present invention relates to a method and system for image processing of an image stream captured by an in-vivo device. More specifically, the present invention relates to systems and methods for detection of transition of the in-vivo device from one gastrointestinal (GI) section to another GI section, for example from the small bowel to the colon. The present invention also relates to systems and methods for changing a mode of operation of an in vivo device in response to such detection.

BACKGROUND

In-vivo measuring systems are known in the art. Some in-vivo devices/systems, which traverse the GI system, include an imaging sensor, or imager, for imaging (e.g., capturing images of) the interior of the GI system. An in-vivo device may include one or more imagers.

Autonomous in-vivo devices traverse the GI system by being moved through the GI system by peristaltic force exerted by the digestive system. While an in-vivo device traverses the GI system, it uses an illumination source to illuminate nearby areas of the GI system, and an optical system and an imaging system to capture images of these areas. In-vivo devices typically include a transmitter for wirelessly transmitting corresponding pictures to an external system where the pictures are processed, for example, to form a displayable video stream. Pictures are typically transmitted as frames. Each frame represents a captured image and contains image data corresponding to the represented captured image. Each frame may also contain metadata that pertains to or is associated with the captured image (e.g., timestamp, decimated image, imaging parameters; e.g., gain and exposure time, color manipulations results) and/or to the in-vivo device (e.g., identification of the in-vivo imager).

Depending on the type of GI problem a patient may be suffering from, a physician may be more interested in a particular GI section. It would, therefore, be beneficial to provide to the in-vivo device and/or to a user, for example a physician, an indication that the in-vivo device has reached a particular GI section, or transitioned from one GI section to another GI section. Such indication may be used, for example, to change the mode of operation of the in-vivo device, to administer a medication, or to facilitate compilation of a video movie from captured images, etc.

SUMMARY OF EMBODIMENTS OF THE INVENTION

An in-vivo device captures images of the GI system and transfers image frames to an external system for analysis. As image frames are transferred from the in-vivo device to the external system, one frame at a time, selected image frames may be rated or scored, possibly in real time or "on the fly". Scoring or rating frames on the fly or in real time may mean that each image frame to be scored/rated is scored/rated by the time the next image frame to be scored/rated is produced by the in-vivo device or by the time the next image frame to be scored/rated is received at the external system, or by any time between these times.

Image data and related non-image data (e.g., metadata) that are contained in each image frame may be analyzed, and a set of features characterizing the pertinent or associated frame and/or image may be extracted. Non-image data may include data that is derived from image data, for example by manipulating image data. Non-image data may be related to image data by, for example, describing the image data, including information on the capture of the image data (e.g., time, device or capsule type or identification, frame order or number) or other information related to the image frame or image. The set of features is evaluated, the evaluation process producing a rating or score $x_i$ (i=1, 2, 3, . . . ,) for the pertinent frame, which is referred to herein as a "frame score". The set of features may be selected or devised such that a transition of the in-vivo device from one GI section to another is made discernible or conspicuous, and detectable by comparing an aggregation of frame scores to a theoretical transition pattern that is referred to herein as the "reference function".

In some embodiments comparing an aggregation of frame scores to a reference function may be implemented by continuously adding or buffering frame scores in a score buffer; shifting the reference function across the currently buffered frame scores n (where n is an integer) frame scores at a time while, after each shift, a difference, or distance, between the reference function and all the currently buffered frame scores is calculated, thus obtaining a sequence of distances {d1, d2, d3, . . . ,}; and searching for a global minimum difference or distance in the sequence of difference or distances {d1, d2, d3, . . . ,}. There is high correlation between the reference function and the frame scores at the global minimum difference or distance, and knowing the reference function and the temporal characteristics of the frame scores and/or of the related frames enables deducing the transition time of the in-vivo device.

If a global minimum difference or distance can be found in the sequence of differences or distances calculated for the currently buffered frame scores, a particular frame score for which the global minimum difference or distance is found may indicate the time at which the in-vivo device transitioned from the particular GI section to the adjacent GI section. Depending on an embodiment, the time at which the in-vivo device transitions from the particular GI section to the adjacent GI section may mean actual time, or time relative to the start of imaging, or both.

If no global minimum difference or distance can be found for the currently buffered frame scores, a new frame is likewise scored; the buffer is updated (e.g., have the frame score added to or buffered in the buffer) with the new frame score; and the reference function may be shifted again across all the frame scores currently held in the updated buffer, thus obtaining an updated sequence of differences/distances. The process including calculation of frame scores, updating of the buffer with the frame scores, and shifting the reference function across the updated buffer may repeat until a global minimum is detected. A particular difference or distance in a sequence of differences/distances may be acknowledged as a 'global minimum difference or distance' only post factum or retroactively; that is, after factoring in additional k (k=

1, 2, 3, . . . ,) frame scores that were calculated/produced after the frame score to which the global minimum difference or distance is attributed.

Knowing the time at which the in-vivo device transitions from a particular GI section to an adjacent GI section may be used, for example, to end a procedure intended for the particular GI section and/or to start a procedure intended for the adjacent GI section, or to change a mode of operation of the in-vivo device as a result of the transition, and/or to administer or release a medication into a target GI section and/or to enable compilation of a video movie from captured images, etc.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 5A demonstrates theoretical groups of frame scores and a reference function according to an example embodiment;

FIG. 5B shows a difference or distance function corresponding to the frame scores and reference function of FIG. 5A;

FIG. 6A demonstrates a realistic spread of frame scores and a reference function according to an example embodiment;

FIG. 6B shows a difference or distance function corresponding to the frame scores and reference function of FIG. 6B;

DETAILED DESCRIPTION

The description that follows provides various details of exemplary embodiments. However, this description is not intended to limit the scope of the claims but instead to explain various principles of the invention and the manner of practicing it.

As explained herein, a frame score may be calculated per image frame or for each image frame. However, a frame score by itself may not provide any correspondence between an image frame and the section of the GI system in which the image frame was captured, but groups or sequences of frame scores, when evaluated or processed as disclosed herein, may allow the detection of transitions of an in-vivo device between GI sections, or the detection that different sequences or groups were captured in different sections of the GI system.

Detection of transition of an in-vivo device from one section of the GI system to another may be performed based on a stream of image frames that are received by the in-vivo device, where each of the image frames may contain an image captured by the in in-vivo device while it traverses the GI tract, and non-image data (e.g., metadata). Frame scores may be calculated for image frames, a frame score per image frame, and a sequence of differences/distances between the frame scores and a reference function may be calculated by shifting the reference function across the frame scores, n frame scores at a time, and, after each shifting, a difference or distance between the frame scores and the reference function may be calculated. Based on the sequence of differences/distances, a particular frame score may be associated with a time at which the in-vivo device transitioned from a first GI section to a second GI section. The reference function may have, for example, a first level, m0, which is associated with the first GI section, and a second level, m1, which is associated with the second GI section.

Figure 1A:
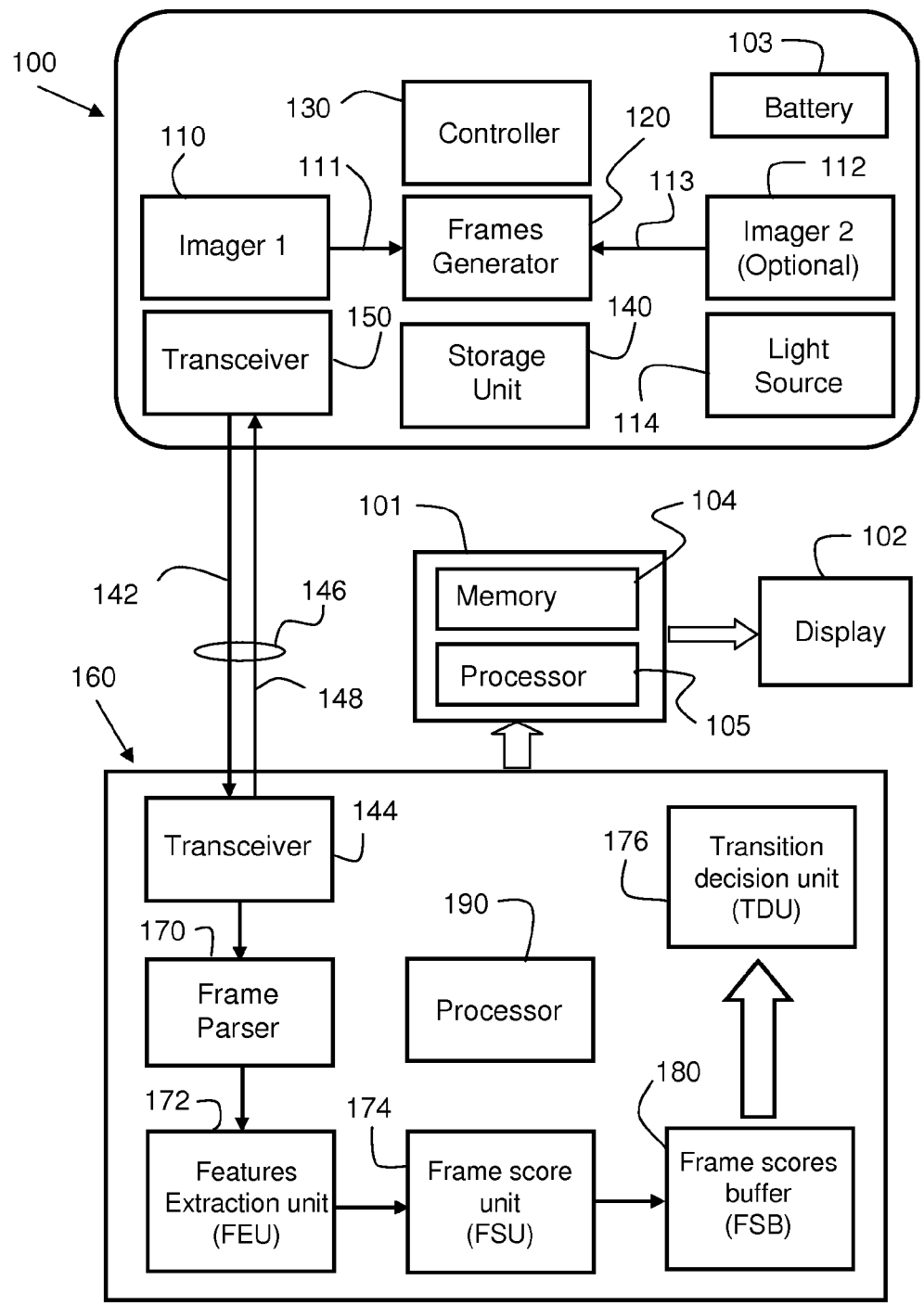
FIG. 1A is a block diagram of an in-vivo imaging system according to an example embodiment.

FIG. 1A schematically illustrates an example in-vivo imaging system. The in-vivo imaging system may include an in-vivo device 100, an external data recorder 160, a workstation 101 (e.g., personal computer), and a display 102. In-vivo device 100 may be, for example a swallowable device, capturing images and transmitting corresponding image frames to an external receiving apparatus, such as data recorder 160. The image frames may, after processing, be compiled or combined into an image stream or video movie for display to a user, for example using display 102.

An in-vivo device may have one or more imagers. One imager, referred to as "front imager", may be situated at the front side of the in-vivo device, and another imager, referred to as "rear imager", may be situated at the rear side of the in-vivo device. A front imager is an imager that views areas ahead of the in-vivo device, whereas a rear imager is an imager that views areas in other directions (e.g., in the opposite direction). Depending on the orientation of the in-vivo device in the GI system, an imager may sometimes function as a front imager and sometimes as a rear imager.

Figure 1B:
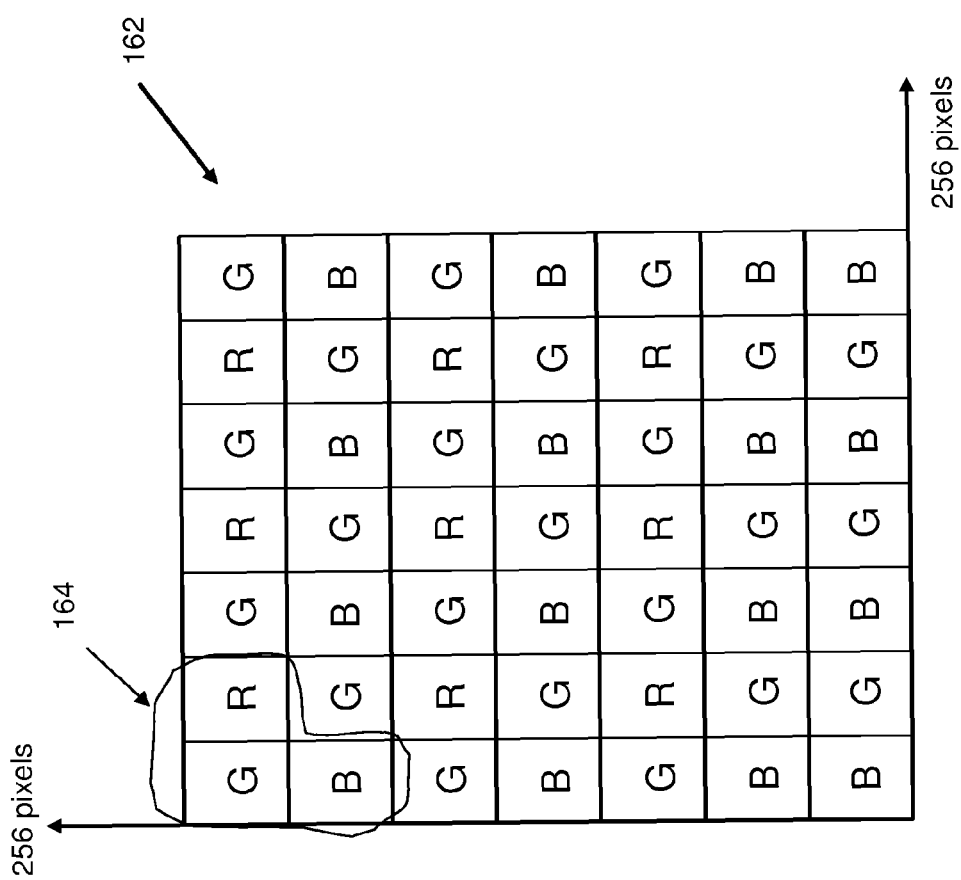
FIG. 1B schematically illustrates an example pixel sampling setup for sampling an image captured by an in-vivo device according to an example embodiment.

An in-vivo device may have one or more imagers and the methodology described herein may be applicable to any imager of the in-vivo device. By way of example, in-vivo device 100 includes two imagers: a first imager 110 and a second imager 112 (numbers of imagers other than one or two may be used, with suitable modifications to the methods discussed herein). According to some embodiments, an imager may include or use an array of 256×256 pixels to capture images, for example as shown in FIG. 1B, though pixels arrays of other sizes and setups, layouts or configurations may be used.

In-vivo device 100 also includes an illumination source 114, a frame generator 120, a controller 130, a storage unit 140, a receiver or transceiver 150, and a power source 103 for powering them. Power source 103 may include one or more batteries, or a charge storing device with electrical circuit that jointly facilitate transfer of electrical power from an external apparatus to the in-vivo device through electromagnetic induction. Controller 130 controllably operates illumination source 114 to illuminate areas traversed by in-vivo device 100, and coordinates the images capturing timing of imagers 110 and 112. Controller 130 may temporarily store captured images and related image frames in storage unit 140. Controller 130 may also perform various calculations and store calculation results in storage unit 140.

At the time of or shortly after in-vivo device 100 is swallowed, or after some predetermined delay (e.g., 2 minutes), imager 110 and imager 112 start capturing images of areas of the GI system. If two imagers are used, such as imager 110 and imager 112, illumination source 114 intermittently illuminates the filed-of-view ("FOV") of one imager at a time while controller 130 concurrently processes the image captured by the other imager. Because natural light does not enter the intestinal tract, imager 110 and imager 112 do not require a light shutter, as opposed to 'regular' (i.e., non-swallowable) imagers. The function of the light shutter is, therefore, implemented by the darkness inside the intestinal tract and by intermittently illuminating the FOV of imager 110, then the FOV of imager 112, then again the FOV of imager 110, etc. Typically, the exposure time of imager 110 and imager 112 is 2-3 milliseconds. If in-vivo device 100 includes both imager 110 and imager 112, in one embodiment, controller 130 operates illumination source 114 such that only one imager can capture an image at any given time. That is, when areas of the intestinal tract which are in front of one imager (e.g., imager 110) are illuminated by illumination source 114, the areas of the intestinal tract which are in front of the other imager (imager 112, to continue the example) remain dark (e.g., not illuminated).

Each of imager 110 and imager 112 includes an image sensor (the image sensors are not shown in FIG. 1A). Each image sensor may be, or include, an array of 256×256 photo sensor elements (e.g., pixels). Imager 110 outputs image data 111 by using a pixel format corresponding to the used pixels. Image data 111 is output for each image that imager 110 captures. Likewise, imager 112 outputs image data 113 by using a pixel format corresponding to the used pixels. Image data 113 is output for each image that imager 112 captures. For convenience, pixels are normally arranged in a regular two-dimensional grid/array. By using this arrangement, many common operations can be implemented by uniformly applying the same operation to each pixel independently. Each image data represents a captured image and, optionally, selected portions thereof.

Frames generator 120 receives image data 111 and, if imager 112 is used, also image data 113, and uses each image data to produce an image frame ("frame" for short) for the pertinent captured image. A frame typically includes a header field that contains information related to the frame itself (e.g., information identifying the frame, the serial number of the frame, the time of production of the frame, the bit-wise length of the frame, etc.). A frame may also include an uncompressed version of the image data and/or a compressed version thereof, and/or suffix data. Suffix data related to a particular captured image may include a decimated image of the captured image and various types of data pertaining to pixels and picture-taking parameters, typically gain value and exposure time, that are involved in the capturing of the image. Suffix data may be 'exported' from in-vivo device 100, for example to data recorder 160, as part of the frames payload. In-vivo device 100 may transfer 142 a frame for each captured image, for example, via wireless communication link 146. While the terms header and suffix is used, metadata contained in these fields can be stored in other places within a frame.

Data recorder 160 may include a receiver or transceiver 144 for receiving frames transferred by in-vivo device 100 and a frame parser 170. Frame parser 170 parses frames in order to extract, from each frame, the uncompressed and/or compressed image and the suffix data, and, from the suffix data, the decimated image associated with or representing the captured image. Data recorder 160 may also include a features extraction unit ("FEU") 172 to extract features from frames and images, a frame score unit ("FSU") 174 to calculate frame scores for frames based on extracted features, and a transition decision unit ("TDU") 176 to determine the time at which in-vivo device 100 transitioned from a particular GI section, in some embodiments the small bowel, to a target GI section, in some embodiments the colon, based on the calculated frames scores. A "frame score" may be thought of as a value that associates the image originating it to a particular GI section.

Data recorder 160 may also include a frame score buffer ("FSB") 180 to buffer frame scores, and a processor 190. FSB 180 may be implemented in hardware or software. For example, FSB 180 may be a memory unit or memory register, or it may be a data structure, a database, etc. Processor 190 may synchronize the operation of frame parser 170, FEU 172, FSU 174, and TDU 176, and analyze buffered frame scores to determine, based on the analysis results, whether or not in-vivo device 100 has transitioned from a particular GI section to a GI section adjacent to the particular GI section. (The adjacent GI section is also referred to herein as a "target section"). While frame scores or ratings are described as being stored in a buffer, other data structures may be used to hold the frame scores, ratings, or other data.

Frame parser 170, FEU 172, FSU 174, and TDU 176 may be implemented in software or in hardware, or partly in hardware and partly in software: they may be dedicated hardware units, or may be code or instructions executed by a controller/processor, e.g., controller 130, processor 190, or processor 105. The code/instructions may be distributed among two or more processors. For example, processor 190, by executing suitable software, code or instructions, may carry out steps which are performed by any one of frame parser 170, FEU 172, FSU 174, TDU 176, and other functions in recorder 160, and thus may function as these units. Data recorder 160 may include additional components (e.g., USB interface, Secure Digital ("SD") card driver/interface, etc.) or units for communicating with a processing/displaying system that is configured to process the images captured by in-vivo device 100 and related data.

In order for processor 190 to determine whether an image was captured in a particular area of the GI system (e.g., in the stomach, small bowel, colon, etc.), various features may be extracted from the raw image (e.g., from the uncompressed image) and from the related non-image data or metadata, and a score, which is referred to herein as a "frame score", may be calculated for a particular frame based on the features extracted or derived from the image data and non-image data pertaining to or associated with the particular frame, and also based on features that were extracted or derived for past frames. When used herein, "past frames" and similar terms, in the context of a sequence of frames, refer to frames captured earlier in time (or the immediately previous in time).

Different images taken from the same GI section usually result in different frame scores. In addition, some frame scores originating from a specific GI section may have values that erroneously associate them with other GI sections (such scores may be thought of as 'stray scores' or 'deviant scores'). Therefore, in one embodiment the resulting frame scores are not used individually to determine that an image was captured in one section of the GI system or another. Instead, the decision regarding the transition of in-vivo device 100 from one GI section to another may be based on statistically discernible groups of frame scores. Since a group of frame scores associated with a specific GI section is statistically distant from a group of frame scores that are associated with, for example, an adjacent GI section, the two groups of frame scores tend to form, over time (e.g., as frames continue to be received), a discernible 'step' that can be used to identify the time at which the in-vivo device transitioned from one GI section to another.

Workstation 101 may include a display or be functionally connected to an external display, for example to display 102. Workstation 101 may receive individual frames from data recorder 160 and produce a video stream for display on, for example, display 102. Workstation 101 may include a memory, such as memory 104, for storing the frames transferred from data recorder 160, and a processor, such as processor 105, for processing the stored frames. The feature extraction process, frame scores calculation process and determining the time at which the in-vivo device transitioned between GI section may be done in any of the workstation 101, data recorder 160, or in-vivo device 100 (e.g., in dedicated units, or in the various processors shown therein), in real time or not. That is, the transition detection methods disclosed herein are also applicable to post-acquisition, non-real time viewing. For example, workstation 101 can present information regarding transitions of in-vivo device 100 between GI sections to a viewer, based on methods disclosed herein.

FIG. 1B schematically illustrates an example pixel sampling setup 162 for sampling an image captured by an in-vivo device according to an example embodiment. Other pixel structures and arrangements may be used. Pixel setup 162 may include multiple triplets of green ("G"), blue ("B") and red ("R") pixels that are arranged as, for example, a Bayer filter mosaic. Other arrangements or mosaics of pixels may be used. An example triplet is shown at 164. Imagers typically use a rectangular shaped array of pixels, for example 256×256 pixels, which result in generally rectangle shaped images.

Capturing an image involves scanning pixels of an image sensor. While pixels are scanned (or afterwards, at a later time), some pixel values are selectively sampled and various calculations are made with respect to them. Pixels' data resulting from the aforesaid sampling process and calculation process may be temporarily held in registers in in-vivo device 100. Other registers in in-vivo device 100 may temporarily hold data pertaining to the gain value and exposure time used in capturing the pertinent image, and these values may change automatically from one captured image to another according to the illumination condition in GI environment the in-vivo device is currently in. Pixel information and gain-exposure data may be transferred to an external system (e.g., data recorder 160) via the suffix data or other metadata included in frames or otherwise associated with images. Extracting features for a particular frame N may involve using image data and non-image data, where the non-image data may include or be derived from image pixels (e.g., summation of red, green and/or blue pixel values, differences of red, green and/or blue pixel values, and other types of manipulations of color pixel values) and gain-exposure information and, optionally, non-imaging information such as environmental information (e.g., temperature, pressure, pH, etc, in the GI system). Extracting features for a particular frame N may also involve manipulation of features that are extracted from previous one or more frames/images.

In some embodiments the features used to calculate frame scores include the features listed in Table-1, which is shown below. In other embodiments other features or additional features may be used to calculate frame scores. Referring to Table-1, 'frame N' denotes a current frame and 'frame N−1', which originates from the same image sensor as frame N−1, denotes a frame preceding or before (in time of acquisition) the current frame. When used herein, "previous", "last" and similar terms, in the context of a sequence of frames, refer to frames captured earlier in time (or the immediately previous in time). Similarly, "next" and similar terms refer to frames captured later in time.

TABLE 1

| Feature no. | Feature name | Description |
|---|---|---|
| 1 | 'absDiffMean_lag1' | Sum of absolute differences between the current frame's decimated image and the last. |
| 2 | 'absDiffMean_lag2' | Sum of absolute differences between the current frame's decimated image and the one before last. |
| 3 | 'absDiffMean_lag3' | Sum of absolute differences between the current frame's decimated image and two before last. |
| 4 | 'absDiffMean_lag1_shift' | 'absDiffMean_lag1' of frame # N − 1 |
| 5 | 'absDiffMean_lag2_shift' | 'absDiffMean_lag2' of frame # N − 1 |
| 6 | 'absDiffMean_lag3_shift' | 'absDiffMean_lag3' of frame # N − 1 |
| 7 | 'absDiffMean_lag1_LP' | Low pass filter over 'absDiffMean_lag1' with coefficients listed below the table. |
| 8 | 'absDiffMean_lag2_LP' | Low pass filter over 'absDiffMean_lag2' |
| 9 | 'absDiffMean_lag3_LP' | Low pass filter over 'absDiffMean_lag3' |
| 10 | 'absDiffMean_minimum' | Minimum over 'absDiffMean_lag1/2/3' |
| 11 | 'absDiffMean_maximum' | Maximum over 'absDiffMean_lag1/2/3' |
| 12 | 'diffSumR_lag1' | abs(SumR(N) − SumR(N − 1)) |
| 13 | 'diffSumG_lag1' | abs(SumG(N) − SumG(N − 1)) |
| 14 | 'diffSumB_lag1' | abs(SumB(N) − SumB(N − 1)) |
| 15 | 'diffDiffR_lag1' | abs(DiffR(N) − DiffR(N − 1)) |
| 16 | 'diffDiffG_lag1' | abs(DiffG(N) − DiffG(N − 1)) |
| 17 | 'diffDiffB_lag1' | abs(DiffB(N) − DiffB(N − 1)) |
| 18 | 'SumR' | Sum of all the red pixels in the imager |
| 19 | 'SumG' | Sum of all the green pixels in the imager |
| 20 | 'SumB' | Sum of all the blue pixels in the imager |
| 21 | 'DiffR' | Sum of absolute differences between red pixels on the imager along the x-axis |
| 22 | 'DiffG' | Same as 'DiffR' on the green pixels |
| 23 | 'DiffB' | Same as 'DiffR' on the blue pixels |
| 24 | 'gainExposure' | Analog gain value times the exposure time of the camera |
| 25 | 'gainExposure_lag1' | gainExposure(N) − 'gainExposure'(N − 1) |

Regarding features 7, 8 and 9, an example low pass filter is shown in formula (1):

$$y(N)=B(1) \cdot x(N)+B(2) \cdot x(N-1)+ \ldots +B(N_B+1) \cdot x(N-N_B) \quad (1)$$

where N is the current index of x, and $N_B$ is the number of elements of B. For example, B may have, in some embodiments, the following values: [0.1817; 01761; 0.1603; 0.1371; 0.1102; 0.0832; 0.0590; 0.0393; 0.0246; 0.0145; 0.0080; 0.0041; 0.0020].

Figure 2:
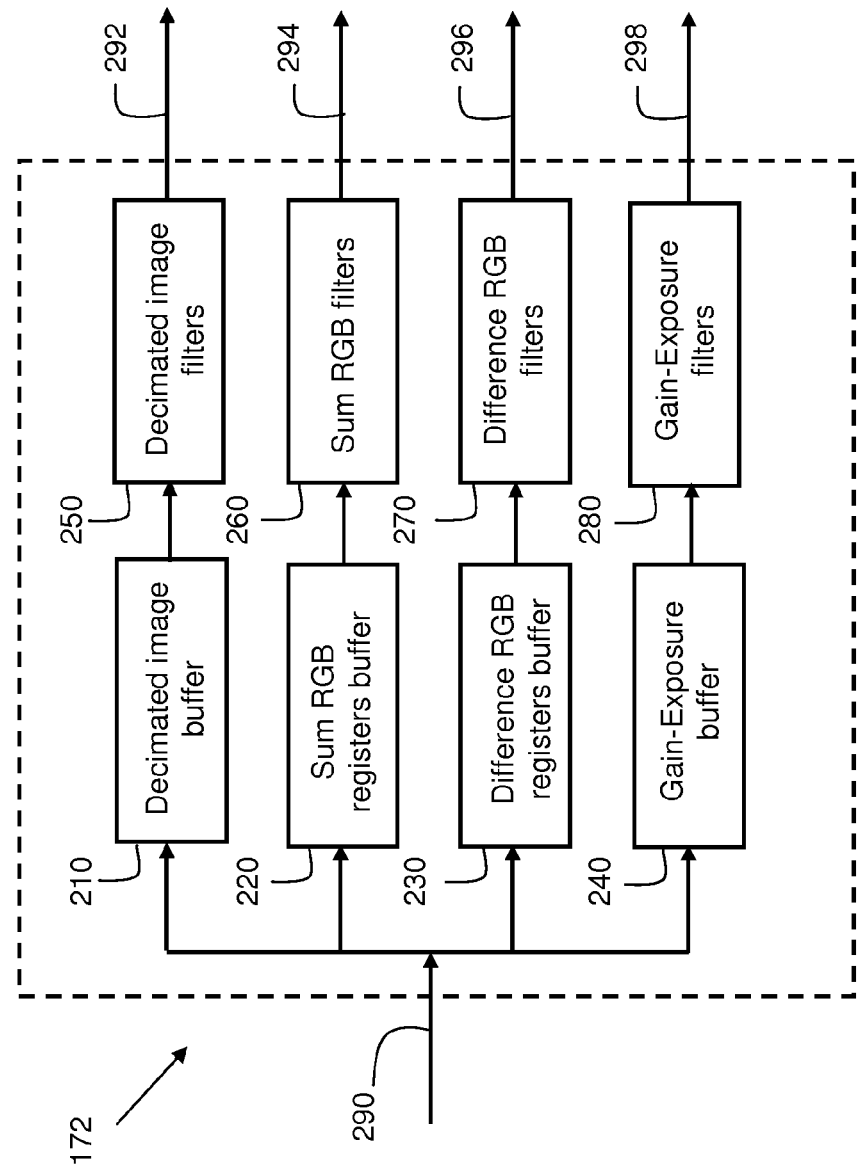
FIG. 2 is a block diagram of a feature extraction unit according to an example embodiment.

FIG. 2 shows a block diagram of features extraction unit (FEU) 172 according to an example embodiment. FEU 172 may include a decimated image buffer 210 and decimated image filters 250, a sum Red-Green-Blue ("RGB") registers buffer 220 and sum RGB filters 260, a differentiation RGB registers buffer 230 and differentiation RGB filters 270, and a gain-exposure buffer 240 and gain-exposure filters 280.

Referring to FIG. 1B, 'Sum RGB' refers to three 'sums': 'SumR', 'SumG', and 'SumB', where 'SumR' is the sum of all the red pixels in the imager; 'SumG' is the sum of all the green pixels in the imager; and 'SumB' is the sum of all the blue pixels in the imager, where each of the sums SumR, SumG, and SumB is held in a separate register buffer. 'Differentiation RGB' refers to three 'differentials': 'DiffR', 'DiffG', and 'DiffB', where 'DiffR' is the sum of absolute differences between red pixels along an axis of the imager; 'DiffG' is the sum of absolute differences between green pixels along an axis of the imager; and 'DiffB' is the sum of absolute differences between blue pixels along an axis of the imager, where each of DiffR, DiffG, and DiffB is held in a separate register buffer. 'Gain-exposure' means the gain value of an imager multiplied by the exposure time of the imager. FEU 172 may be based on, or use, the aforesaid Sum RGB, Differentiation RGB and gain-exposure features as is and to derive from them additional features as shown, for example, in Table-1 above. In other embodiments other features extraction units may be used.

The data used for the manipulation of the pixel information and the gain-exposure information may be obtained from the suffix data 290 or other metadata of one or more frames, as the case may be. For example, feature no. 3 in Table-1 uses information from suffix data of the last three frames. Decimated image filters 250 outputs features 1 through 11 (inclusive) in Table-1, the output being shown at 292; sum RGB filters 260 output features 12-14 and 18-20 in Table-1, the output being shown at 294; difference RGB filters 270 output features 15-17 and 21-23 in Table-1, the output being shown at 296; and gain-exposure filters output features 24 and 25 in Table-1, the output being shown at 298.

Figure 3:
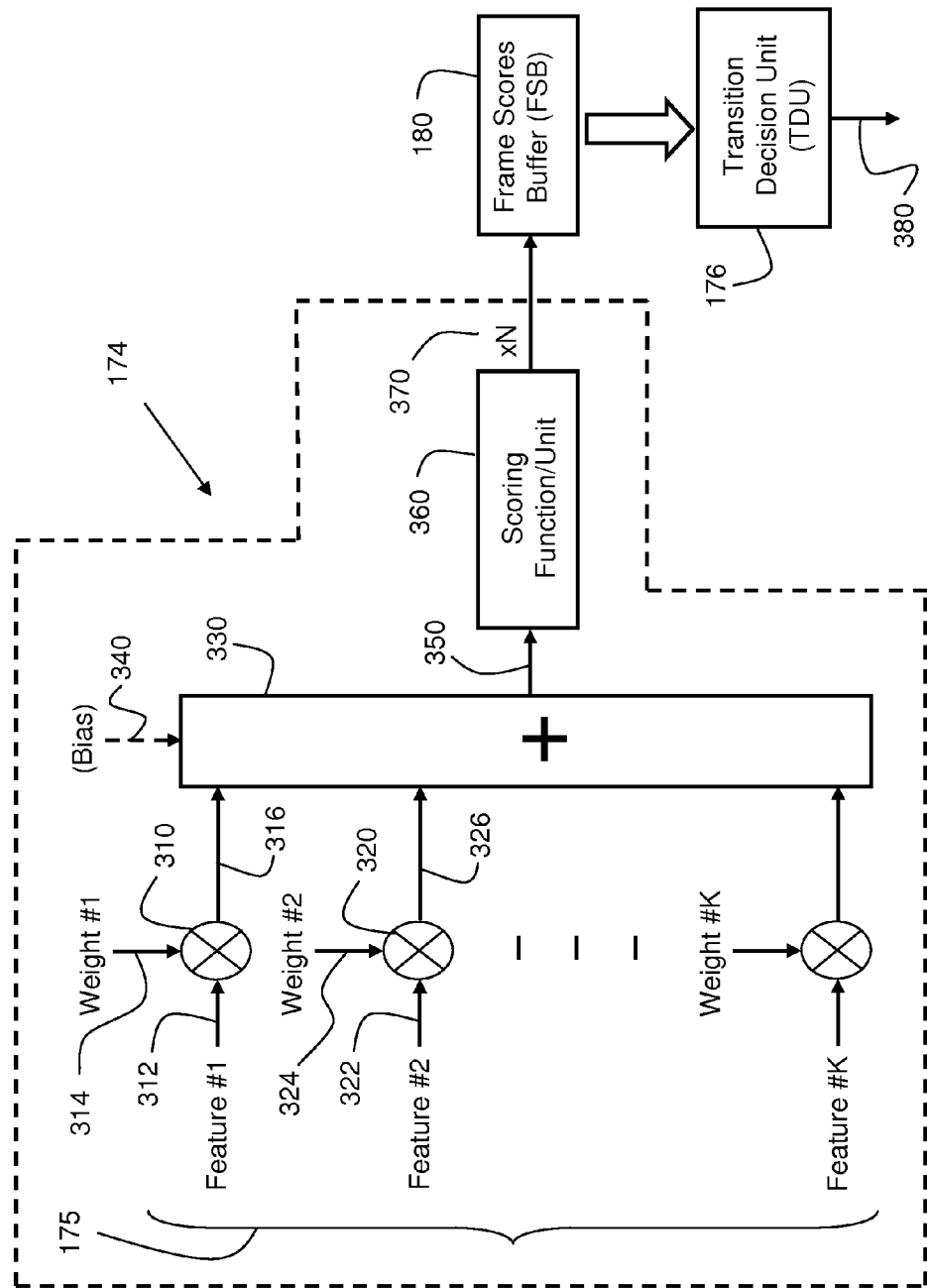
FIG. 3 is a block diagram of a frame score unit according to an example embodiment.

FIG. 3 shows a block diagram of frame score unit (FSU) 174 according to an example embodiment. Frame score unit (FSU) 174 may include k 'feature branches' 175 that may include k multipliers, such as multipliers 310 and 320, to multiply each of k features by an associated weight. FSU 174 may also include an adder 330 and a scoring function, or scoring unit, 360 for rating, or scoring, images based on features that may be extracted from the images. In other embodiments other frame score functions/units may be used. Each multiplier may be uniquely assigned to a specific feature type. K may be equal to 25, which is the number of the exemplary features in Table-1. For example, multiplier 310 may be assigned to feature 1 in Table-1; multiplier 320 may be assigned to feature 2 in Table-1, and so on.

The features specified in Table-1 may be extracted, for example, as shown in FIG. 2, and used to calculate a frame score or rating for each frame. Other embodiments may use less than 25 features, or more than 25 features, or other features. In one embodiment, scoring function 360 may be, include, or implement a logistic linear classifier, which is a type of linear classifier, to calculate frame scores. The logistic linear classifier may be based, for example, on logistic function (2); in other embodiments other classifiers may be used.

$$Y(\alpha) = \frac{1}{1 + e^{-\alpha}} \quad (2)$$

In one embodiment frame scores may be calculated by using formula or scoring function (3):

$$x_N = \frac{1}{1 + e^{-\sum_{j=1}^{k}[w(j)f(j)]-b}} \quad (3)$$

where $x_N$ is a frame score calculated for frame N, f(j) is feature j (where j=1, 2, . . . , k, where k is the number of features), w(j) is a weight assigned to feature f(j), and b is a constant bias.

The value of $x_N$ can theoretically be within the range 0-1. The weights, w(j), may be obtained through training of the system, for example by using a sequence of training frames, or training data. Processor 190 may include or be configured (e.g., provided with a code or instructions) to implement the classifier (e.g., logistic linear classifier, scoring function (3), etc.).

FIG. 3 shows one way for implementing formula (3): multiplier 310 multiplies the first feature (shown at 312) by weight #1 (shown at 314); multiplier 320 multiplies the second feature (shown at 322) by weight #2 (shown at 324), and so on. Adder 330 adds up the k multiplication results 316, 326, etc. and optionally a bias 340, and outputs 350 a 'feature' sum to score function/unit 360. Score function/unit 360 outputs a frame score, $x_N$ (shown at 370), that corresponds to frame N. The frame score, $x_N$, is, then, buffered in frame scores buffer (FSB) 180. As new frame scores are calculated for frames on the fly, and FSB 180 is continuously updated with such scores, transition decision unit (TDU) 176 continuously analyzes the frame scores buffered in FSB 180, for example by calculating a difference or distance between buffered frame scores and a reference function, in order to output 380 a signal, message, or indication regarding the time or frame identified as the transition time/frame at which in-vivo device 100 transitioned from one GI section of interest to another GI section of interest.

The features used to calculate frame scores may be selected such that the values of frame scores—excluding values of stray/deviant frame scores—are limited to a score range corresponding to, or associated with, the GI section that originates the frame scores. That is, given suitable features, as in-vivo device 100 traverses a particular GI section, frame scores corresponding to the particular GI section may tend to reside within a distinct score range corresponding to the particular GI section, though some frame scores may be out of that range. One way for transition decision unit (TDU) 176 to distinguish between score ranges, and thus between the respective GI sections, is by using a reference function. A reference function may be a function that enables calculation of a difference or distance between frame scores to distinct levels or ranges associated with distinct different GI sections. Example reference functions are shown, for example, in FIGS. 4A, 4B, and 4C, which are described below.

Figure 4A:
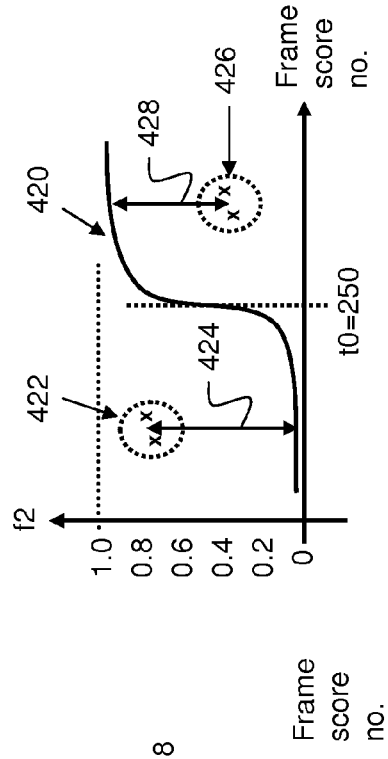
FIGS. 4A, 4B, 4C show reference functions according to some example embodiments.
Figure 4B:
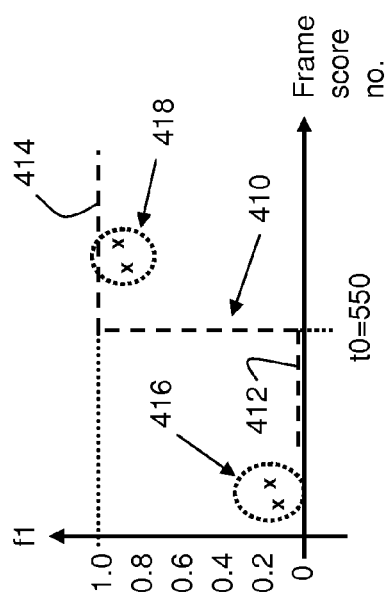
Figure 4C:
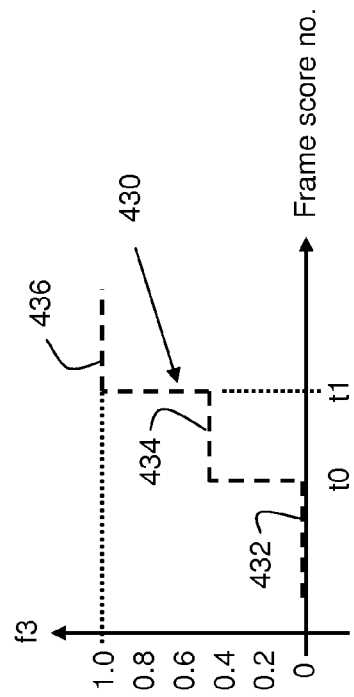

FIGS. 4A, 4B and 4C show reference functions for detecting transition of an in-vivo device from one GI section to another according to some example embodiments. Referring to FIG. 4A, it shows an example reference function or step function 410. Step function 410 may be defined as:

$$f_{t0}(i) = \begin{cases} 0, & i < t0 \\ 1, & i \geq t0 \end{cases} \quad (4)$$

where i (i=1, 2, 3, . . . , N) is the index of the frame score, and $t_o$ is the "ascending point" of step function 410.

An 'ascending point' of a reference function is a point where the reference function steeply or moderately ascends from one distinct level of the reference function to another distinct level. An 'ascending point' of a reference function may be a point that resides in-between, or separates between, two distinct levels of a reference function. A reference function having q distinct levels, where each of the q distinct levels is associated with a distinct GI section or subsection, has q−1 ascending points.

For example, reference function 410 includes 2 levels: level '0', which is shown at 412, and level '1', which is shown at 414. The set of features shown in Table-1 have been chosen to detect transition of in-vivo device 100 from the small bowel to the colon, and such that frame scores originating from the small bowel would have relatively low values corresponding, for example, to level '0', and frame scores originating from the colon would have higher values that correspond, for example, to level '1'.

Frame scores may be calculated at the rate at which images are captured and frames are transmitted, or at a different rate. For brevity, only four frame scores are shown in FIG. 4A, two of which (shown at 416) are originated from a first GI section (e.g., small bowel), and the other two (shown at 418) are originated from a second GI section (e.g., colon). Transition of an in-vivo device from the first GI section to the second GI section may be determined by placing the ascending point of step function 410 at different frame score numbers and calculating, for each frame score number, the difference or distance between reference function 410 and the frame scores. For example, the ascending point of reference function 410 is shown in FIG. 4A placed at frame number 550 (i.e., t0=550). Since step function 410 has two levels (e.g., '0' and '1'), it may be referred to as a '2-level' step function. In general, placing the ascending point of step function 410 at different frame score numbers, etc. means placing the ascending point at a first frame score, calculating a first difference or distance, d1, between the frame scores to step function 410; then moving the ascending point n (n=1, 2, 3, . . . ,) frame scores away, to a second frame score, and calculating a second difference or distance, d2, between the frame scores to step function 410, and so on.

The difference or distance between frame scores 416 and 418 and reference function 410 is relatively short because frames scores 416 are relatively close to level '0' of function 410 and frames scores 418 are relatively close to level '1' of function 410. Therefore, the instance $t_0=550$ ('550' being an example frame number/index at which the ascending point of function 410 is placed) may, according to this example, be used as an indication for a transition of an in-vivo device from the GI section corresponding to the '0' level to the GI section corresponding to the '1' level.

FIG. 4B shows a curved 2-level step function 420. Frame scores 422 are relatively distant from level '0' of function 420 (an approximated difference or distance is shown at 424), and frames scores 426 are relatively distant from level '1' of function 420 (an approximated difference or distance is shown at 428). Therefore, the difference or distance between frame scores 422 and 426 to step function 420 is relatively long, the ascending point, t0, of step function 420 may be shifted a couple of or a few times, n frame scores at a time (e.g., to frame score number 255, then to frame score number 260, and so on), until a frame score is found, which results in a global minimum difference or distance. As explained above, a local minimum difference or distance can be thought of as a global minimum difference or distance only after frame scores that follow the local difference or distance are also factored in.

FIG. 4C shows a 3-level step function 430. Step function 430 may be defined as shown in formula (5):

$$f_{t0,t1}(i) = \begin{cases} 0, i < t0 \\ 0.5, t0 \le i < t1 \\ 1, i \ge t1 \end{cases} \quad (5)$$

where i (i=1, 2, 3, . . . , N) is the index of the frame score, $t_0$ is a first ascending point of step function 430, and $t_1$ is a second ascending point of step function 430.

Step function 430 has a '0' level (shown at 432), which may be associated with a first GI section (e.g., stomach), a '0.5' level (shown at 434), which may be associated with a second GI section (e.g., small bowel), and a '1' level (shown at 436), which may be associated with a third GI section (e.g., colon). Using the aforesaid three associations, step function 430 may enable determining that an in-vivo device is in the stomach, or in the small bowel, or in the colon, or, equivalently, that it has transitioned from the stomach to the small bowel, or from the small bowel to the colon. A reference function may have any suitable number of levels and not necessarily two levels or three levels, and levels of a reference function may have values other than '0', '0.5' and '1'. In other embodiments other reference functions may be used.

FIG. 5A shows a theoretical case where a group of consecutive frame scores, which are numbered 1 to 16, have a value '0', and another group of consecutive frame scores, which are numbered 17 to 36, have a value '1'. Each frame score in FIG. 5A is shown as an 'x'. Reference function 510 has a low level (e.g., level '0') and a high level (e.g., level '1'). The low level of reference function 510 may be set to '0' but it is shown slightly above frame scores 1 to 7, as shown at 512, in order not to obscure the drawing. Likewise, the high level of reference function 510 may be set to '1' but it is shown slightly below frame scores 8 to 36, as shown at 514, in order not to obscure the drawing. Assume that 36 frames were received (i.e., N=36), for example by data recorder 160, and a buffer, such as frame scores buffer 180, currently holds corresponding 36 frame scores. Also assume that a 2-level step function 510, an example reference function, is initially placed at frame number 7 (e.g., $t_0$ in formula (4) equals to 7).

The difference or distance, $F(t_0)$, of a group of frame scores from a reference function, $f_{t_0}$, may be calculated by using formula (6):

$$F(t_0) = \sum_{i=1}^{N} (f_{t0}(i) - x_i)^2 \quad (6)$$

where N is the number, or group, of frame scores currently held in a frame scores buffer, and $x_i$ is the score value of a frame score indexed i in the N frame scores.

Applying formula (6) to the 36 frame scores of FIG. 5A while the ascending point of step function 510 is placed at the 7th frame score yields:

$F(t_0=7)=7\times(0-0)^2+9\times(1-0)^2+20\times(1-0)^2=0+9+0=9$

Because '9' (the result above corresponding to $F(t_0=7)$) is the first difference or distance calculated and a global minimum difference or distance value of $F(t_0)$) is searched for, the ascending point of step function 510 is to be shifted a predetermined frame scores to the right hand side. For brevity, assume that the ascending point of step function 510 is shifted, or moved, (520) to frame score number 17. By "shifted" or "moved" in one embodiment a reference function is moved such that the function's ascending point coincides with, or placed at, a next target frame score which, in this example, is frame score number 17, before the formula (e.g., formula (6)) is reapplied or reused. In some embodiments, the reference function is not physically moved, and rather what is meant by placing or moving the reference function is that when the formula is applied, it is applied to the same set of data (e.g., set of frame scores) for every target frame score, but each time with the ascending point placed at a different target frame score. Reapplying formula (6) to the 36 frame scores after the shift; e.g., for $F(t_0=17)$ yields:

$$F(t_0=17)=16\times(0-0)^2+20\times(1-1)^2=0+0=0$$

In order to ensure that the value of $F(t_0=17)$ is a global minimum difference or distance, the ascending point of step function 510 should be shifted a few more frame scores, and if no smaller frame scores can be found, $F(t_0=17)$ may be regarded, with relatively high certainty, as the searched for global minimum difference or distance. For the sake of simplicity, assume that ascending point of step function 510 is shifted (530) to frame number 26. Reapplying formula (6) to the 36 frame scores for $F(t_0=26)$ yields:

$$F(t_0=26)=16\times(0-0)^2+9\times(0-1)^2+11\times(1-1)^2=0+9+0=9$$

From the calculations above it may be concluded that the function $F(t_0)$ has a global minimum difference or distance when the ascending point of step function 510 is placed at the $17^{th}$ frame score. Saying that $F(t_0)$ has a global minimum difference or distance when the ascending point of step function 510 is placed at or in proximity to the $17^{th}$ frame score is equivalent to saying that the difference or distance between the frame scores shown in FIG. 5A and reference function 510 has a global minimum when the ascending point of reference function 510 is placed at or in proximity to frame score number 17. Therefore, the time at which the $17^{th}$ frame score was received may indicate, in some embodiments to processor 190 (in other embodiments to controller 130 directly or indirectly e.g., by processor 190), that the in-vivo device has transitioned from a GI section (e.g., small bowel) associated with the low level (e.g., '0') of step function 510, to a GI section (e.g., colon) associated with the high level (e.g., '1') of step function 510. In reality, frame scores associated with the same GI section may be scattered as demonstrated in FIG. 6A. FIG. 5B shows a difference or distance function 540 corresponding to the theoretical case of FIG. 5A. The example value calculated for $t_0=7$ (e.g., 9) is shown at 550; the example value calculated for $t_0=17$ (e.g., 9) is shown at 560, and the example value calculated for $t_0=26$ (e.g., 26) is shown at 570. As FIG. 5B demonstrates, difference or distance function 540 has a local minimum difference or distance at $t_0=17$, which is also a global minimum difference or distance, but it has no other local minimum differences/distances.

Referring again to FIG. 3, the value of output 370 depends on the type of scoring function 360, and, therefore, it does not necessarily have to be in the range 0-1. In some embodiments, scoring function 360 may be a logistic function. Scoring function 360 may output frame scores whose values may fall within, or vary between, unknown range m0-m1, where m0 and m1 may, respectively, be the lowest limit of the scoring function and the highest limit of the scoring function. For example, m0 may equal to, say, 0.55, and m1 may equal to, say, 3.55. Formula (4) may, accordingly, be generalized according to formula (7):

$$f_{t0,m0,m1}(i) = \begin{cases} m0, & i < t0 \\ m1, & i \geq t0 \end{cases} \quad (7)$$

In some embodiments m0<m1 and in other embodiments m0>m1. By way of example m0=0 and m1=1. In some embodiments the values of m0 and m1 may be predetermined and in other embodiments the values of m0 and m1 are not predetermined and may be known only post factum or retroactively.

Formula (6) may also be generalized as demonstrated by formula (8):

$$F(t_0, m0, m1) = \sum_{u=1}^{N} |f_{t0,m0,m1}(i) - x_i|^P \quad (8)$$

where P is an integer.

FIG. 6A shows two score ranges 612 and 632 that are respectively associated with a first GI section and a second GI section. While frame scores 610, which are associated with the first GI section, are all reside in the score range 612 associated with that GI section, frame scores 620 are stray/deviant scores. While frame scores 630, which are associated with the second GI section, are contained within the score range 632 associated with the second GI section, frame scores 640 are stray/deviant scores. The higher the number of the stray frame scores, the harder the detection of the transition time/frame. Therefore, the features to be extracted from the captured images may be selected in such a way that the number of stray/deviant frame scores is reduced to an acceptable level that enables detection of the transition time/frame. Therefore, despite the stray frame scores, the time/frame at which the in-vivo device transitions from the first GI section to the second GI section may still be detected by shifting a reference function, for example reference function 650 or a similar function, across the frame ratings or frame scores. Shifting a reference function across N frame scores may include placing the ascending point of the reference function at a first frame score and calculating a first difference or distance, d1, between the frame scores and the reference function, then placing the ascending point of the reference function at a second frame score and calculating a second difference or distance, d2, between the frame scores and the reference function, and so on, until the ascending point of the reference function is positioned at the last ($N^{th}$) frame score of the N frame scores. Shifting a reference function across N frame scores may produce a sequence of up to N differences/distances, depending on the shifting interval; e.g., shifting the reference function n frame scores at a time and calculating a difference or distance, di (i=1, 2, 3, ...,), for every $n^{th}$ frame score. When used herein, shifting or placing may describe in visual or geometric terms, or metaphorically, the operations of a computer or processor comparing or otherwise processing functions and other data, and thus the function may not be literally moved, placed or shifted.

FIG. 6B shows a distance function 660 corresponding to FIG. 6A. As FIG. 6B demonstrates, distance function 660 has a local minimum distance at 670 and another local minimum distance at 680. The local minimum distance at 670, which is detected before the local minimum distance at 680, is initially estimated to be the function's global minimum distance. In order to determine whether the local minimum distance at 670 is, indeed, the function's global minimum distance, the distance function 660 has to be evaluated, or checked, for another time period (e.g., one to two minutes after the time corresponding to the minimum at 670) in order to provide a better perspective regarding the behavior of function 660. Therefore, additional frame scores are factored in (e.g., frame scores 8 to 13). Since distance function 660 generally decreases during period 690, the distance minimum 670 is not regarded as a global minimum distance.

As discussed above, a particular distance in a sequence of distances may be acknowledged as a 'global minimum distance' only post factum or retroactively; that is, after factoring in additional k frame scores that were calculated/produced after the frame score to which the global minimum distance is attributed. To that extent, a determination that local minimum distance 680 is also a global minimum distance may be made after shifting the reference function k frame scores away from frame score number 17; for example five frame scores (e.g., k=5) away (e.g., at a time 692 corresponding to frame score number 22). After a predetermined time period T elapses since point 680 (e.g., at point 692), it may be concluded that distance function 660 is approximately convex shaped, with its lowest point/value obtained for frame score 17. Local minimum distance 680 can be regarded as the searched for global minimum distance because distance function 660 generally increases from that point.

As demonstrated by FIG. 6B, a distance function may have more than one local minimum, one of which is the function's global minimum distance. One way to determine whether a particular local minimum distance is also a global minimum distance is by checking the value of the distance function a predetermined time, Tm, elapses from the particular local minimum distance. Referring to FIG. 6B, in order to check whether local minimum distance 670 is also the function's global minimum distance, the function's value is rechecked again after time period Tm (shown at 694) elapses from the time at which frame score 7 was calculated. Because the frames' transfer rate is known, the number of received frames is translatable into elapsed time. Therefore, saying that m frames were received is equivalent to saying that a time corresponding to the reception of the m frames has elapsed. Therefore, the notation "i (frame score no.)" of the horizontal (e.g., 'X') axis may be equivalently replaced by a time notation.

Because the function's value at point 672 is lower than local minimum 670, it is concluded that local minimum 670 is not a global minimum and, therefore, another local minimum is checked in the same way. In order to check whether local minimum distance 680 is the function's global minimum, the function's value may be rechecked again after time Tm (shown at 696) elapses since the time at which frame score 17 was calculated. Because the function's value at point 682 is higher than local minimum 680, it may be concluded that local minimum 680 is the global minimum of distance function 660. The wider Tm, the higher the certainty that local minimum 680 is the global minimum of distance function 660.

The length of time period Tm (shown at 694 and 696) may change as per the application. For example, if the in-vivo device is to perform a mode change by releasing a medication in a particular GI section, it may be beneficial to use a relatively long Tm (e.g., 10 minutes); and if the in-vivo device is to reversibly change an image capturing rate as a result of the detection of the global minimum distance, it may be beneficial to use a relatively shorter Tm (e.g., to 2 to 5 minutes). Depending on the application, the decision that a local minimum distance is also a global minimum distance may result in a reversible consequence (e.g., reversibly changing the mode of operation of the in-vivo device), or in irreversible consequence (e.g., releasing a medication into a GI section). That is, if, at a given time, a local minimum distance is determined to be global, and later (e.g., after time Tm elapses) the distance function has a lower value, the decision that the local minimum was the function's global minimum distance may be revoked. As a result of the decision revocation, to the extent possible, actions made in response to the decision may be undone. For example, a current image capturing rate may be replaced by a previously used rate.

Figure 7:
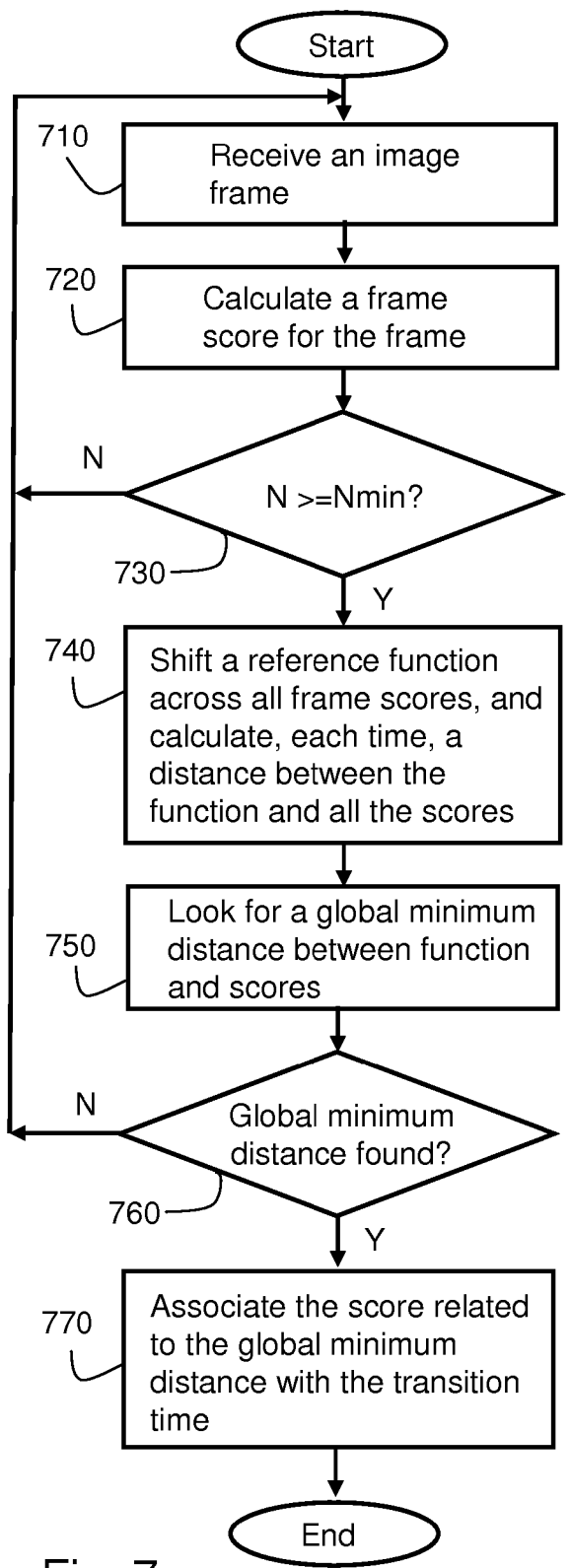
FIG. 7 shows a flowchart of a method for detecting the transition time of an in-vivo device from a particular GI section to another GI section according to an example embodiment.

FIG. 7 is a flowchart of a method for detecting the transition time of an in-vivo device from a particular GI section to another GI section according to an example embodiment. While in one embodiment such a method may be performed by the system shown in FIG. 1A, other systems may perform methods of the present invention. At step 710, an image frame is received, for example at data recorder 160, and, at step 720, a frame score is calculated for the received frame, for example by FSU 174, and stored in a frame score buffer, for example in FSB 180. Processor 190, by executing suitable software, code or instructions, may carry out steps which are performed by FSU 174, and thus may function as this unit.

Assume that a reference function is provided, which has a first level, m0, associated with a first GI section, and a second level, m1, associated with a second GI section. In some embodiments m0 and m1 may be known in advance. In other embodiments their values may be found, for example by processor 190, for example, by averaging the frame scores on both sides of $t_0$; e.g., averaging the frame scores on the left hand side relative to $t_0$ to find m0, and averaging the frame scores on the right hand side relative to $t_0$ to find m1. Also assume that N frame scores are currently buffered, for example by processor 190, for example in FSB 180. The frame scores held in FSB 180 may be processed, and the distance between the processed frame scores and a reference function may be calculated. For example, processing the frame scores may include calculating a median for the buffered frame scores.

At step 730 it is checked, for example by processor 190, whether N is equal to or greater than a minimum number of frame scores, Nmin (e.g., $N_{min}$>5). If less than Nmin frame scores are currently buffered; i.e., N<Nmin (shown as "N" at step 730), shifting the reference function across the buffered frame scores may result in an indecisive or erroneous transition determination result. Therefore, the procedure used to determine the transition time/frame may start or commence only after a sufficient number of frame scores are buffered; i.e., for N≥Nmin.

If at least $N_{min}$ frame scores are already buffered (shown as "Y" at step 730), the reference function is stepwise shifted, at step 740, across the buffered frame scores n (n=1, 2, 3, etc.) frame scores at a time, and, after each shift of n frame scores, the distance between the N frame scores and the shifted reference function is (re)calculated, thus obtaining a sequence of distances that increases in time, as image frames continue to be received. The reference function may be shifted across the buffered frame scores by, for example, transition decision unit (TDU) 176. Processor 190, by executing suitable software, code or instructions, may carry out steps which are performed by TDU 176, and thus may function as this unit. In order to shorten the recalculation process mentioned above, a distance currently calculated for frame scores may be updated for a new frame score by factoring in a new difference between the new frame score and the shifted reference function, and by recalculating only differences for frame scores whose position relative to $t_0$ has changed as a result of the shifting of the reference function. That is, if the reference function is shifted, say, n frames, there is no need to recalculate differences between frame scores and the reference function if the position of these frame scores relative to $t_0$ has not changed as a result of the shifting of the reference function.

At step 750, a global minimum distance is searched for in the sequence of distances calculated at step 740, and at step 760 it is checked, for example by processor 190, whether a global minimum distance has been detected. If no global minimum distance can be found in the current sequence of distances (shown as "N" at step 760), the steps 710 and 720 are repeated in order to update the buffer with an additional frame score, and the steps 740 and 750 are applied on the content (i.e., frame scores) of the updated buffer. Steps 410 through 750 may repeat until a global minimum distance is detected. If a global minimum distance is detected (shown as "Y" at step 760), it may be deemed that a transition is detected. At step 770, the frame score related to or originating the global minimum distance, or the frame associated with that frame score, may be associated, for example by processor 190, with the transition time; i.e., the time at which the in-vivo device transitioned between the GI sections involved.

Knowing the time at which the in-vivo device transitions from a particular GI section to an adjacent GI section allows, for example, changing a mode of operation of the in-vivo device. In some embodiments, changing the mode of operation of the in-vivo may include ending a procedure intended for the particular GI section and/or starting a procedure intended for the adjacent GI section, or changing the image capturing rate of the in-vivo device as a result of the transition, or instructing or prompting a user to do something, for example to swallow a medication. For example, medication may be released from the in-vivo device into a specific GI section but not to other GI sections; or a first medication may be released from the in-vivo device into a first GI section and a second medication may be released from the in-vivo device into a second GI section, etc. In some embodiments, processor 190 may send an instruction to controller 130 to release the medication(s) and/or to change the images capturing rate. In other embodiments, controller 130, in conjunction with other units similar to the units used by data recorder 160, may independently detect the section transition time and respond accordingly to perform, after the transition, in a way that is suitable for the GI section of interest, e.g., suitable for the second GI section.

Referring to step 730, the number of frame scores, N, held in the buffer may be increased each time a new frame score is calculated, and the reference function may be shifted across all N frame scores or across some of the N frame scores. Other operations or sequence of operations may be used.

As explained above, the global minimum of the distance between frame scores and a reference function coincides, within a clinically usable margin, with the actual transition time. The distance function may also have local minimum distances. Therefore, in order to ensure that a minimum distance is a global one, additional (e.g., 'post-transition') frame scores may be calculated and taken into account. In other words, the determination that a sequence of distances has a global minimum distance at a particular frame score may be made some (e.g., k) frames 'away' from, or, equivalently, a certain time period after, the particular frame score to ensure, with high certainty, that a detected minimum distance is also the searched for global minimum distance. By way of example, k may correspond to a time period Tm that is equal to 1 minute, 2 minutes, etc. Using post-transition frame scores to confirm a global minimum distance defers the determination regarding the transition detection. Referring again to FIG. 6B, Tm may be selected as a tradeoff between transition certainty and delayed transition detection; the longer the detection delay, the higher the detection certainty.

Figure 8:
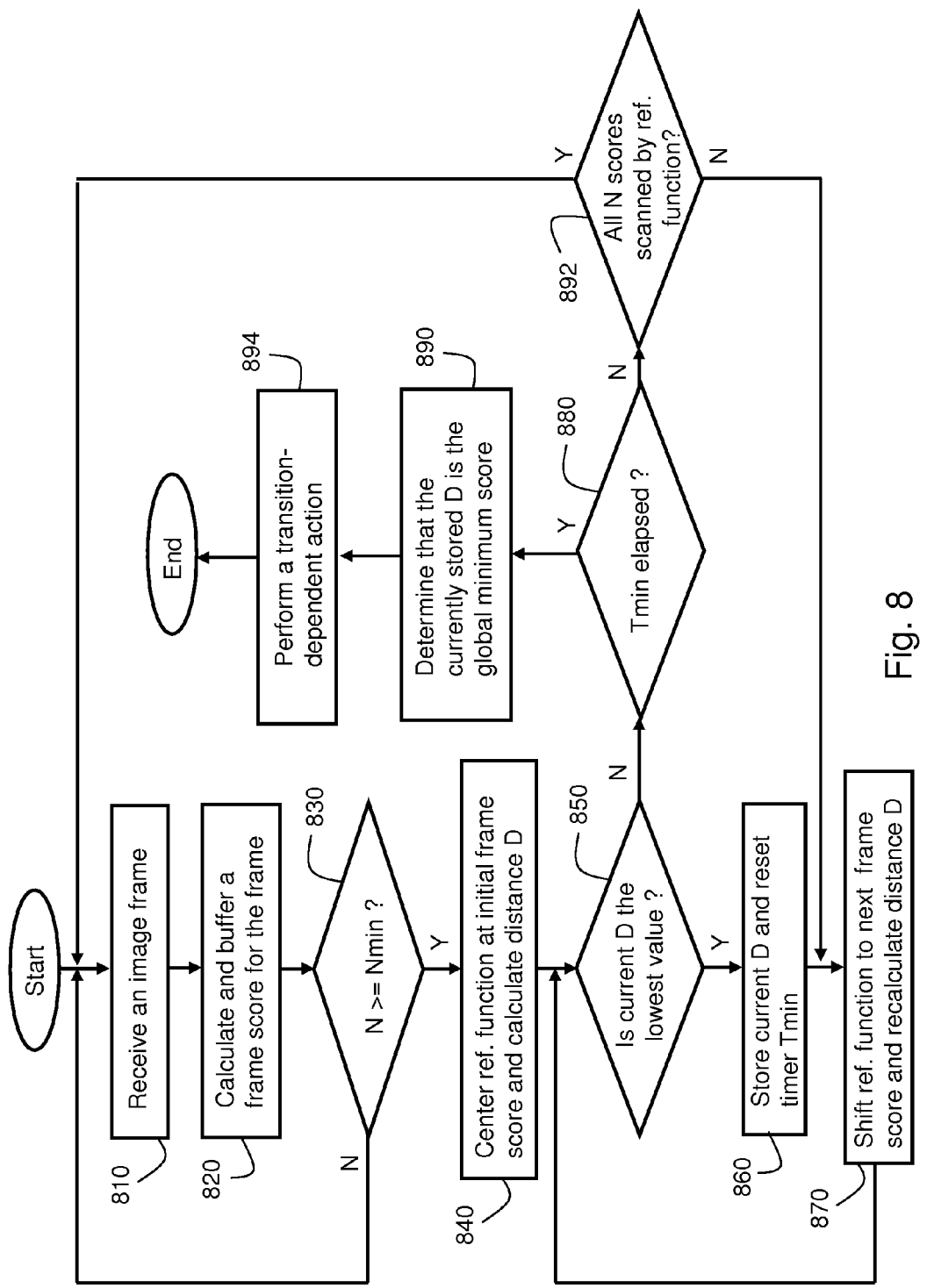
FIG. 8 shows a flowchart of a method for detecting the transition time of an in-vivo device from a particular GI section to another GI section according to another example embodiment.

FIG. 8 is a flowchart of a method for detecting the transition time of an in-vivo device from a particular GI section to another GI section according to another example embodiment. While in one embodiment such a method may be performed by the system shown in FIG. 1A, other systems may perform methods of the present invention. Assume that a Tmin timer starts running. At step 810, an image frame is received, for example by transceiver 144 of FIG. 1A, and at step 820 a frame score is calculated, for example by FSU 174, for the received image frame and held in a frame scores buffer such as FSB 180.

At step 830 it is checked, for example by TDU 176, whether the buffer holding frame scores contains at least a minimum number, Nmin, of frame scores. If the frame scores buffer contains less than Nmin frame scores (shown as "N" at step 830), another frame is received (at step 810), and a score is calculated for it and buffered (at step 820). If the frame scores buffer contains at least Nmin frame scores (shown as "Y" at step 830), the process of calculating the distance between all the buffered frame scores and a reference function may start or commence. Accordingly, at step 840, the reference function (e.g., the function's COM) is located, for example by TDU 176, at an initial frame score, for example at the 30$^{th}$ frame score, and the distance, D, between the buffered frame scores and the reference function is calculated, for example by TDU 176, for that location.

At step 850, it is checked, for example by TDU 176, whether the current distance D is the minimum distance calculated so far. If it is determined that the current distance D is the minimum distance calculated so far (shown as "Y" at step 850), then at step 860 the current value of D is temporarily stored in a memory and the (free-running) timer Tmin is reset. When the first distance D is calculated, it is assumed that it is the global minimum of the distance function. Therefore, it is stored in the memory and the measurement of the time period Tmin starts by resetting the free-running timer Tmin.

At step 870, the reference function is shifted to a new location (e.g., to another frame score), for example by TDU 176, and the distance, D, between all the buffered frame scores and the shifted reference function is recalculated at step 850 for the new location. The reference function may be shifted n frame scores at a time. If the new distance D is smaller than the previously calculated distance, this may indicate that the distance function descends. Therefore, at step 860, the old distance D in the memory is replaced by the new distance D, and the timer Tmin is reset. Steps 870, 850 and 860 are performed every time a distance D is found, which is smaller than the currently stored distance. By performing steps 870, 850 and 860, the memory is updated at any given time with the lowest distance D found by that time, and the time period, Tmin, is zeroed with each such updating.

Referring to step 850, if it is determined that the currently calculated distance D is larger than the stored distance D (shown as "N" at step 850), the timer Tmin is permitted to run, to measure Tmin, and it is checked, at step 880, whether the time period Tmin has elapsed. If the time period Tmin has not elapsed (shown as "N" at step 880), it is checked, at step 892, whether all the N frame scores were 'scanned' by the reference function. By 'completely scanned by a reference function' is meant that the reference function is shifted across all the intended frame scores within the current N frame scores. If an additional shift can be performed with respect to the current N frame scores (shown as "N" at step 892), the reference function is shifted to the next frame score, at step 870, and step 850 is rechecked. If all the planned shifts were exhausted with respect to the current N frame scores (shown as "Y" at step 892), a new image frame is processed at steps 810 and 820, and the Nnew frame scores (Nnew=N+1) are started to be scanned by the reference function at step 840; step 850 is rechecked with respect to the Nnew frame scores, etc.

Referring to step 880, if the time period Tmin has elapsed (shown as "Y" at step 880), this means that (at step 890) the minimum distance D that was stored last in the memory is, with high probability, the searched for global minimum distance. Therefore, the time at which the last minimum distance D was calculated or stored, or the time at which the pertinent image frame was received, may indicate the transition time. At step 894 it may be decided, for example by processor 190, to perform a transition-dependent action, such as refraining from performing certain activities, performing specified activities, changing the mode of operation of the in-vivo device, changing the image capturing rate of the in-vivo device, display a message or indication to a user (e.g., physician) regarding, for example, the time or frame identified as the transition time/frame, etc., or other information regarding the transition. Processor 190, by executing suitable software, code or instructions, may carry out steps which are performed by any one of FSU 174 and TDU 176, and other functions in recorder 160, and thus may function as these units. Other operations or sequence of operations may be used.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of multiple embodiments.

Embodiments of the invention may include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein.

Having thus described exemplary embodiments of the invention, it will be apparent to those skilled in the art that modifications of the embodiments will be within the scope of the invention. Alternative embodiments may include more modules, fewer modules and/or functionally equivalent modules. In particular, scoring frames, calculating the distance between frame scores and a reference function, determining transition to a GI section, and determining the operation mode of in-vivo device 100 may be performed, mutatis mutandis, by in-vivo device 100. In addition, the transition detection methods disclosed herein are applicable to real time applications as well as to post-acquisition, non-real time applications. For example, the determination regarding transition of an in-vivo device to a GI section of interest can be done long after the image frames are scored, or the image frames can be scored long after they are generated by the in-vivo device or transferred by the in-vivo device to the external system.

The invention claimed is:

1. A method for detecting transition of an in-vivo device from one section of the gastrointestinal system to another, comprising:
   receiving a stream of image frames, each of the image frames comprising an image captured by an in in-vivo device traversing the GI tract and related non-image data;
   calculating frame scores, a frame score for each image frame;
   calculating a sequence of distances between the frame scores and a reference function, $f$, by shifting the reference function across the frame scores and, after each shifting, calculating a distance between the frame scores and the reference function, wherein calculating a distance comprises calculating a difference between all frame scores and the shifted reference function; and
   associating, based on the sequence of distances, a particular frame score with a time at which the in-vivo device transitioned from a first section of the gastrointestinal system to a second section of the gastrointestinal system.

2. The method as in claim 1, comprising, for each currently received image frame,
   calculating the frame score based on features extracted from the image and from non-image data in the frame, and from image data and non-image data in past image frames;
   buffering the frame score in a frame score buffer;
   calculating the sequence of distances by shifting the reference function across frame scores that are buffered in the frame score buffer; and
   determining whether the sequence of distances has a global minimum distance at the particular frame score, and if the sequence of distances has a global minimum distance at the particular frame score, associating the particular frame score with the time at which the in-vivo device transitioned from the first gastrointestinal section to the second gastrointestinal section, and if the sequence of distances resulting from the buffered frame scores does not have a global minimum distance at any currently buffered frame score,
   (i) receiving a new image frame;
   (ii) calculating and buffering a frame score for the new image frame;
   (iii) recalculating a new sequence of distances for the buffered frame scores;
   (iv) determining whether the new sequence of distances has a global minimum distance; and
   if the new sequence of distances does not have a global minimum distance,
   repeating steps (i) to (iv) until a global minimum distance is identified.

3. The method as in claim 2, wherein the determination that the sequence of distances has a global minimum distance at the particular frame score is made after shifting the reference function k frame scores away from the particular frame score.

4. The method as in claim 2, wherein shifting the reference function across the currently buffered frame scores starts after buffering at least $N_{min}$ frame scores in the frame scores buffer, wherein $N_{min}>5$.

5. The method as in claim 2, wherein the reference function $f$ is defined as:

$$f_{t0,m0,m1}(i) = \begin{cases} m0, & i < t0 \\ m1, & i \geq t0 \end{cases}$$

where $t_0$ is an ascending point of the reference function, m0 is a first level associated with the first gastrointestinal section, and m1 is a second level associated with the second gastrointestinal section.

6. The method as in claim 5, wherein m0<m1.

7. The method as in claim 5, wherein m0 and m1 are predetermined.

8. The method as in claim 5, wherein m0 and m1 are not predetermined.

9. The method as in claim 5, wherein the distance between the currently buffered frame scores and the reference function is calculated by using a function $F(t_0, m0, m1)$ defined as:

$$F(t_0, m0, m1) = \sum_{i=1}^{N} |f_{t_0,m0,m1}(i) - x_i|^P$$

where i (1≤i≤N) is an index of the frame score, N is the number, or group, of the frame scores buffered in the frame score buffer, $x_i$ is a score value of a frame score indexed i, and P is an integer.

10. The method as in claim 9, wherein P is selected from the group consisting of 1 and 2.

11. The method as in claim 1, further comprising performing a transition dependent action selected from the group consisting of: changing a mode of operation of the in-vivo device, changing an image capturing rate of the in-vivo device, releasing a medication, refraining from performing certain activities, performing specified activities, displaying a message for a user regarding the time or frame identified as the transition time/frame, and instructing or prompting a user to swallow a medication.

12. The method as in claim 1, wherein the first gastrointestinal section is any one of: (i) the stomach, (ii) the small bowel, and (iii) the colon.

13. The method as in claim 1, wherein the second gastrointestinal section is any one of: (i) the stomach, (ii) the small bowel, and (iii) the colon.

14. The method as in claim 1, wherein the first gastrointestinal section and the second gastrointestinal section are adjacent sections.

15. The method as in claim 1, wherein the reference function is a step function $f$.

16. A method for detecting transition of an in-vivo device from one section of the gastrointestinal system to another, the method comprising:

for a stream of image frames, each of the frames comprising an image captured by an in in-vivo device traversing the gastrointestinal tract and related non-image data, calculating a frame score for each image frame;
calculating a sequence of distances between the frame scores and a reference function, $f$, by shifting the reference function across the frame scores and, after each shifting, calculating a distance between the frame scores and the reference function, wherein calculating a distance comprises calculating a difference between all frame scores and the shifted reference function; and
associating a particular frame score with a time at which the in-vivo device transitioned from a first GI section to a second GI section based on the sequence of distances.

17. A system for detecting transition of an in-vivo device between sections of the gastrointestinal system, comprising:
a receiver to receive a stream of image frames from an in-vivo device traversing the gastrointestinal system, each of the image frames comprising an image of the gastrointestinal system captured by the in-vivo device and related non-image data;
a processor configured to,
calculate frame scores, a frame score for each image frame;
calculate a sequence of distances between the frame scores and a reference function by,
(i) shifting the reference function across the frame scores and, after each shifting,
(ii) calculating a distance between the frame scores and the reference function, wherein calculating a distance comprises calculating a difference between all frame scores and the shifted reference function; and
associate a particular frame score with a time at which the in-vivo device transitioned from a first section of the gastrointestinal system to a second section of the gastrointestinal system, based on the sequence of distances.

18. The system as in claim 17, wherein the processor is to extract features from images and related non-image data to facilitate calculation of a frame score.

19. The system as in claim 17, wherein the particular frame score associated with the time at which the in-vivo device transitioned from the first section of the gastrointestinal system to the second section of the gastrointestinal system is a frame score for which the sequence of distances has a global minimum distance.

20. The system as in claim 19, further comprising a frame score buffer to buffer frame scores, wherein the processor is to determine whether a sequence of distances resulting from buffered frame scores has a global minimum distance at the particular frame score, and if the sequence of distances has a global minimum distance at the particular frame score,
associate the particular frame score with the time at which the in-vivo device transitioned from the first gastrointestinal section to the second gastrointestinal section, and if the sequence of distances resulting from the buffered frame scores does not have a global minimum distance at any buffered frame score,
(i) receive a new image frame;
(ii) calculate and buffer a frame score for the new image frame;
(iii) recalculate a new sequence of distances for the buffered frame scores;
(iv) determine whether the new sequence of distances has a global minimum distance; and
if the new sequence of distances does not have a global minimum distance,
repeat operations (i) to (iv) until a global minimum distance is identified.

* * * * *